(12) United States Patent
Marliere

(10) Patent No.: US 8,703,455 B2
(45) Date of Patent: Apr. 22, 2014

(54) PRODUCTION OF VOLATILE DIENES BY ENZYMATIC DEHYDRATION OF LIGHT ALKENOLS

(71) Applicant: Scientist of Fortune, S.A., Luxembourg (LU)

(72) Inventor: Phillippe Marliere, Mouscron (BE)

(73) Assignee: Scientist of Fourtune, S.A., Luxembourg (LU)

( * ) Notice: Subject to any disclaimer, the term of this patent is extended or adjusted under 35 U.S.C. 154(b) by 0 days.

(21) Appl. No.: 13/957,482

(22) Filed: Aug. 2, 2013

(65) Prior Publication Data

US 2014/0065686 A1 Mar. 6, 2014

(30) Foreign Application Priority Data

Aug. 29, 2012 (EP) ..................... 12182270

(51) Int. Cl.
*C12P 5/02* (2006.01)
*C12N 9/00* (2006.01)
*C12N 1/20* (2006.01)
*C12N 15/00* (2006.01)

(52) U.S. Cl.
USPC ..... 435/167; 435/183; 435/252.3; 435/320.1; 536/23.2

(58) Field of Classification Search
None
See application file for complete search history.

(56) References Cited

FOREIGN PATENT DOCUMENTS

| WO | WO 2011/076689 | 6/2011 |
|---|---|---|
| WO | WO 2011/076691 | 6/2011 |
| WO | WO 2012/177439 | 12/2012 |
| WO | WO2013/028519 | 2/2013 |
| WO | WO 2013/082542 | 6/2013 |
| WO | WO2013/173437 | 11/2013 |

OTHER PUBLICATIONS

Accession E1XUJ2. Sep. 5, 2010.*
Chica et al. Curr Opin Biotechnol. Aug. 2005;16(4):378-84.*
Sen et al. Appl Biochem Biotechnol. Dec. 2007;143(3):212-23.*
Brodkorb et al. J Biol Chem. Oct. 1, 2010;285(40):30436-42.*
WO 2013/090915; Braskem S.A., International Publication Date: Jun. 20, 2013.
U.S. Appl. No. 61/576,788.
U.S. Appl. No. 61/606,035.
International Search Report and Written Opinion for PCT/EP2013/067727, dated Oct. 29, 2013.
Brodkorb et al: "Linalool Dehydratase-Isomerase, a Bifunctional Enzyme in the Anaerobic Degradation of Monoterpenes", The Journal of Biological Chemistry, vol. 285:40 (2010), pp. 30436-30442. 1-4.
De Malde: "A New Process for the Industrial Synthesis of Isoprene", Platinum Metals Review, vol. 7, 1963, p. 152.
Vavilov et al: "Synthesis of Isoprene from 1,3-Dioxolane and Isobutylene", Russian Journal of Applied Chemistry, vol. 83 (2010) pp. 1598-1601.
Luddeke et al: "Geraniol and Geranial Dehydrogenases Induced in Anaerobic Monoterpene Degradation by Castellaniella defragrans", Applied and Environmental Microbiology, vol. 78, (2012), pp. 2128-2136.
Luddeke et al: "Genetic Evidence for a Second Anaerobic Monoterpene-Activating Enzyme in Castellaniella defragrans", Biospektrum (special edition), Mar. 2012, p. 181 (Retrieved from the Internet: URL:http://www.vaam.de/tl files/vaam/Tagungen/Tagungsband 2012.pdf).
Fall: "Microbial Production of Isoprene", Progress Report: DE-FG03-97ER20274, 2002, pp. 1-4, XP002714853, Retrieved from the Internet: URL:http://www.osti.gov/scitech/servlets/purl/792551.
Brodkorb et al, "Linalool Dehydratase-Isomerase, a Bifunctional Enzyme in the Anaerobic Degradation of Monoterpenes", The Journal of Biological Chemistry, vol. 285: 30436-30442, 1-4. (2010).
De Malde, "A New Process for the Industrial Synthesis of Isoprene", Platinum Metals Reviews, vol. 7: 152 (1963).
Vavilov et al., "Synthesis of Isoprene from 1,3-dioxolane and isobutylene", Russian Journal of Applied Chemistry, vol. 83: 1598-16-1 (2010).
European Search Report received in EP 12 182 270.4 on Feb. 14, 2013.
U.S. Appl. No. 61/688,514, Glycos Biotechnologies, Inc.
U.S. Appl. No. 61/776,485, Glycos Biotechnologies, Inc.

* cited by examiner

*Primary Examiner* — Christian Fronda
(74) *Attorney, Agent, or Firm* — Michele M. Wales; InHouse Patent Counsel, LLC

(57) ABSTRACT

Described is a method for generating conjugated dienes through a biological process. More specifically, the application describes a method for producing conjugated dienes (for example butadiene, isoprene or dimethylbutadiene) from light alkenols via enzymatic dehydration, in particular by making use of an alkenol dehydratase.

28 Claims, 10 Drawing Sheets

|    | Structure | | | | |
|----|-----------|---|---|---|---|
| #5 | HO-CH(H)-C(H)=CH₂ with CH₃ | STA | H | H | butadiene |
| #6 | HO-C(H)(CH₃)-C(CH₃)=CH₂ | STA | CH₃ | H | isoprene |
| #7 | H₃C-C(OH)(H)-C(H)=CH₂ with CH₃ | STA | H | CH₃ | isoprene |
| #8 | H₃C-C(OH)(CH₃)-C(CH₃)=CH₂ | STA | CH₃ | CH₃ | dimethyl-butadiene |

5 but-3-en-2-ol
6 3-methylbut-3-en-2-ol
7 2-methylbut-3-en-2-ol
8 2,3-dimethylbut-3-en-2-ol

Figure 2

| | | PHA | R1 | R2 | Product |
|---|---|---|---|---|---|
| #9 | but-3-en-1-ol / isocrotyl alcohol | PHA | H | H | butadiene |
| #10 | 2-methylbut-3-en-1-ol | PHA | CH3 | H | isoprene |
| #11 | 3-methylbut-3-en-1-ol / isoprenol | PHA | H | CH3 | isoprene |
| #12 | 2,3-dimethylbut-3-en-1-ol | PHA | CH3 | CH3 | dimethyl-butadiene |

Figure 3

MRFTLKTTAIVSAAALLAGFGPPPRAAELPPGRLATTEDYFAQQAKQAVTPDVMAQLAYM
NYIDFISPFYSRGCSFEAWELKHTPQRVIKYSIAFYAYGLASVALIDPKLRALAGHDLDI
AVSKMKCKRVWGDWEEDGFGTDPIEKENIMYKGHLNLMYGLYQLVTGSRRYEAEHAHLTR
IIHDEIAANPFAGIVCEPDNYFVQCNSVAYLSLWVYDRLHGTDYRAATRAWLDFIQKDLI
DPERGAFYLSYHPESGAVKPWISAYTTAWTLAMVHGMDPAFSERYYPREKQTFVEVYDEG
RKARVRETAGTDDADGGVGLASAFTLLLAREMGDQQLFDQLLNHLEPPAKPSIVSASLRY
EHPGSLLFDELLFLAKVHAGFGALLRMPPPAAKLAGK

Figure 6

SEQUENCE LISTING

<160> NUMBER OF SEQ ID NOS: 1

<210> SEQ ID NO 1
<211> LENGTH: 397
<212> TYPE: PRT
<213> ORGANISM: Castellaniella defragrans

<400> SEQUENCE: 1

```
Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
            35                  40                  45

Val Thr Pro Asp Val Met Ala Gln Leu Ala Tyr Met Asn Tyr Ile Asp
        50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
            115                 120                 125

Arg Val Trp Gly Asp Trp Glu Glu Asp Gly Phe Gly Thr Asp Pro Ile
        130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr Asp Tyr
        210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
            275                 280                 285

Phe Lys Gln Thr Phe Val Glu Val Tyr Asp Glu Gly Arg Lys Ala Arg
        290                 295                 300

Val Arg Glu Thr Ala Gly Thr Asp Asp Ala Asp Gly Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu His Pro Gly Ser Leu Leu Phe
        355                 360                 365
```

```
Asp Glu Leu Leu Phe Leu Ala Lys Val His Ala Gly Phe Gly Ala Leu
    370                 375                 380

Leu Arg Met Pro Pro Pro Ala Ala Lys Leu Ala Gly Lys
385                 390                 395
```

PRODUCTION OF VOLATILE DIENES BY ENZYMATIC DEHYDRATION OF LIGHT ALKENOLS

This Application is a continuation of EP 12 18 2270.4 which was filed on Aug. 29, 2012. The entire contents of EP 12 18 2270.4 are hereby incorporated by reference in its entirety.

The present invention relates to a method for generating conjugated dienes, in particular volatile dienes, through a biological process. More specifically, the invention relates to a method for producing butadiene, isoprene or dimethylbutadiene from light alkenols via enzymatic dehydration, in particular by making use of an alkenol dehydratase.

Conjugated dienes, e.g. 1,3-dienes such as butadiene or isoprene, are important molecules for the industry. Isoprene (2-methyl-1,3-butadiene) is a conjugated diene with the formula $C_5H_8$. It, is a key compound for the tire industry, and also has many applications in the adhesives. It is produced chemically using several routes:

Extractive distillation from oil (C5 cut)
Dehydrogenation of iso-amylene
Double dehydrogenation of isopentane
Reaction of isobutene and formaldehyde
Reaction of acetone and acetylene
Propylene dimerization WO 2009/076676 reports a metabolic pathway to isoprene. The pathway is based on the dephosphorylation-dehydration of downstream intermediates in the mevalonate pathway, i.e. isoprenyl-pyrophosphate or prenyl-pyrophosphate. This process has the drawback of requiring going through the whole mevalonate pathway: double phosphorylation of mevalonate, followed by a decarboxylation-dehydration into isoprenyl-pyrophosphate, further isomerised into prenyl-pyrophosphate, and finally double dephosphorylation/dehydration into isoprene.

Butadiene (1,3-butadiene) is a conjugated diene with the formula $C_4H_6$. It is an important industrial chemical used as a monomer in the production of synthetic rubber, nylon, ABS (Acrylonitrile-butadiene-styrene), plastics, latex. There exist different possibilities to produce butadiene. Butadiene is, for example, produced as a by product of the steam cracking process used to produce ethylene and other olefins. In this process butadiene occurs in the C4 stream and is normally isolated from other byproducts by extraction into a polar aprotic solvent, such as acetonitrile, from which it is then stripped. Butadiene can also be produced by the catalytic dehydrogenation of normal butane or it can be produced from ethanol. In the latter case, two different processes are in use. In a single-step process, ethanol is converted to butadiene, hydrogen and water at 400-450° C. over a metal oxide catalyst (Kirshenbaum, I. (1978), Butadiene. In M. Grayson (Ed.), *Encyclopedia of Chemical Technology*, 3rd ed., vol. 4, pp. 313-337. New York: John Wiley & Sons). In a two-step process, ethanol is oxidized to acetaldehyde which reacts with additional ethanol over a tantalum-promoted porous silica catalyst at 325-350° C. to yield butadiene (Kirshenbaum, I. (1978), loc cit.). Butadiene can also be produced by catalytic dehydrogenation of normal butenes.

For the past two decades, genetic engineering technologies have made possible the modification of the metabolism of micro-organisms, and hence their use to produce key substances which they would otherwise produce at a low yield. By enhancing naturally occurring metabolic pathways, these technologies open up new ways to bio-produce numerous compounds of industrial relevance. Several industrial compounds such as amino-acids for animal feed, biodegradable plastics or textile fibres are now routinely produced using genetically modified organisms.

There is still a need to provide environmentally friendly, cost efficient and simple methods for producing the above-mentioned compounds.

The present application addresses this need by the provision of the embodiments as specified in the claims.

The present invention is based on the design of a novel biocatalyst for the synthesis of volatile diene compounds, in particular conjugated dienes such as 1,3-dienes, based on the conversion of light alkenols, in particular by the enzymatic dehydration of light alkenols. The invention is based on the demonstration that said conversion can be carried out biologically by using an enzyme catalyzing a dehydration reaction. The invention can be implemented in vitro, in cell-free systems, or by using organisms, in particular microorganisms. The invention also relates to the production of conjugated dienes such as 1,3-dienes from a carbon source, and particularly a carbohydrate (in particular glucose), a polyol (in particular glycerol), a biodegradable polymer (in particular starch, cellulose, poly-3-hydroxyalkenoate) the carbon source being converted by a microorganism to a light alkenol, which is then converted to a conjugated diene such as a 1,3-diene.

More specifically, the invention relates to a method for producing a conjugated diene characterized in that it comprises a step of enzymatically converting a compound responding to the general formula $C_nH_{2n}O$ into $C_nH_{2n-2}$+ $H_2O$, with 3<n<7, by making use of an alkenol dehydratase. The conversion is a dehydration.

A compound responding to the formula $C_nH_{2n}O$, with 3<n<7, is referred to in the context of the present invention as a light alkenol. In one preferred embodiment n is 4. In this case, the light alkenol to be used as a substrate in the method according to the invention responds to the formula $C_4H_8O$. Compounds which respond to this formula are but-2-en-1-ol (crotyl alcohol), but-3-en-2-ol and but-3-en-1-ol (isocrotyl alcohol). The diene which results from the conversion of these compounds according to the method of the present invention is butadiene. In a particularly preferred embodiment the light alkenol used as a substrate in the method according to the invention is but-2-en-1-ol (crotyl alcohol) or but-3-en-2-ol and the produced diene is butadiene.

In another preferred embodiment n is 5. In this case, the light alkenol to be used as a substrate in the method according to the invention responds to the formula $C_5H_{10}O$. Compounds which respond to this formula are 2-methylbut-2-en-1-ol, 3-methylbut-2-en-1-ol (prenol), 3-methyl but-3-en-2-ol, 2-methylbut-3-en-2-ol, 2-methylbut-3-en-1-ol and 3-methylbut-3-en-1-ol (isoprenol). The diene which results from the conversion of these compounds according to the method of the present invention is isoprene. In a particularly preferred embodiment the light alkenol used as a substrate in the method according to the invention is 3-methylbut-2-en-1-ol (prenol) or 2-methylbut-3-en-2-ol and the produced diene is isoprene.

In another preferred embodiment n is 6. In this case, the light alkenol to be used as a substrate in the method according to the invention responds to the formula $C_6H_{12}O$. Compounds which respond to this formula are 2,3-dimethylbut-2-en-1-ol, 2,3-dimethylbut-3-en-2-ol and 2,3-dimethylbut-3-en-1-ol. The diene which results from the conversion of these compounds according to the method of the present invention is dimethyl-butadiene.

The compounds responding to the general formula $C_nH_{2n}O$, with $3<n<7$, can be subdivided into three groups, namely into (i) primary allyl alcohols (PRA) of the formula I:

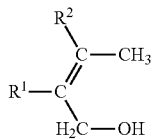

Formula I (ii) secondary or tertiary allyl alcohols (STA) of the formula II:

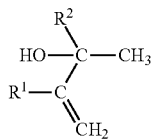

Formula II and (iii) primary homoallyl alcohols (PHA) of the formula III:

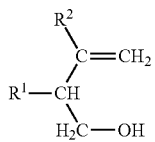

Formula III wherein $R^1$ and $R^2$ are independently selected from H and $CH_3$.

In one preferred embodiment, the compound responding to the general formula $C_nH_{2n}O$, with $3<n<7$, is a primary allyl alcohol (PRA) of the formula I:

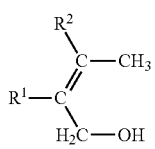

Formula I wherein $R^1$ and $R^2$ are independently selected from H and $CH_3$. Compounds responding to this formula are but-2-en-1-ol (crotyl alcohol), 2-methylbut-2-en-1-ol, 3-methylbut-2-en-1-ol (prenol) and 2,3-dimethylbut-2-en-1-ol (see FIG. 1). In one preferred embodiment, the primary allyl alcohol is but-2-en-1-ol (crotyl alcohol) and the produced diene is butadiene. In another preferred embodiment, the primary allyl alcohol is 3-methylbut-2-en-1-ol (prenol) and the produced diene is isoprene.

In another preferred embodiment, the compound responding to the general formula $C_nH_{2n}O$, with $3<n<7$, is a secondary or tertiary allyl alcohol (STA) of the formula II:

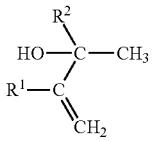

Formula II wherein $R^1$ and $R^2$ are independently selected from H and $CH_3$. Compounds responding to this formula are but-3-en-2-ol, 3-methylbut-3-en-2-ol, 2-methylbut-3-en-2-ol and 2,3-dimethylbut-3-en-2-ol (see FIG. 2).

In one preferred embodiment, the STA is but-3-en-2-ol and the produced diene is butadiene. In another preferred embodiment, the STA is 2-methylbut-3-en-2-ol and the produced diene is isoprene.

In a further preferred embodiment, the compound responding to the general formula $C_nH_{2n}O$, with $3<n<7$, is a primary homoallyl alcohol (PHA) of the formula III:

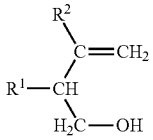

Formula III wherein $R^1$ and $R^2$ are independently selected from H and $CH_3$. Compounds responding to this formula are but-3-en-1-ol (isocrotyl alcohol), 2-methylbut-3-en-1-ol, 3-methylbut-3-en-1-ol (isoprenol) and 2,3-dimethylbut-3-en-1-ol (see FIG. 3). In one preferred embodiment, the homoallyl alcohol is 3-methylbut-3-en-1-ol (isoprenol) and the produced diene is isoprene.

FIG. 4 gives a schematic overview over the conversion of the above mentioned PRA, PHA and STA compounds into a conjugated diene according to the method of the present invention.

If reference is made in the context of the present invention to a compound of which there exist stereoisomers, e.g. because of Z/E inversions at the sp2 C═C double bonds or because of R/S inversions at the chiral sp3 C centers, all these stereoisomers are encompassed by reference to such a compound. For example, the mention of but-2-en-1-ol (crotyl alcohol) refers to the cis (Z) as well as to the trans (E) stereoisomer and the mention of 3-methylbut-3-en-2-ol refers to both the R and S isomer.

As described above, the method according to the present invention is characterized in that the conversion of the compound responding to the general formula $C_nH_{2n}O$ into $C_nH_{2n-2}+H_2O$, with $3<n<7$, is achieved by using an alkenol dehydratase. An alkenol dehydratase is an enzyme which can dehydrate an alkenol, preferably, it is an enzyme which can dehydrate at least one compound responding to the general formula $C_nH_{2n}O$, with $3<n<7$, and wherein the product of the reaction is $C_nH_{2n-2}+H_2O$. This activity can be measured in assays as described in the appended Examples. An example of an alkenol dehydratase to be employed in a method according to the present invention is the alkenol dehydratase which has been designated "linalool dehydratase-isomerase" and which has been identified in *Castellaniella defragrans* (formerly

*Alcaligenes defragrans*) strain 65Phen (Brodkorb et al., J. Biol. Chem. 285 (2010), 30436-30442). Linalool dehydratase-isomerase is a bifunctional enzyme which is involved in the anaerobic degradation of monoterpenes. The native enzyme has been found to have a molecular mass of 160 kDa and is assumed to be a homotetramer of 40 kDa subunits. The enzyme catalyzes in vitro two reactions in both directions depending on the thermodynamic driving forces. On the one hand, the enzyme catalyzes the isomerisation of the primary allylalcohol geraniol into its stereoisomer linalool which bears a tertiary allyl alcohol motif. On the other hand, the enzyme catalyzes the water secession (dehydration) from the tertiary alcohol linalool to the corresponding acyclic monoterpene beta-myrcene, a molecule bearing a conjugated diene motif. FIG. 5 gives an overview of the reactions catalyzed by linalool dehydratase-isomerase in vitro under anaerobic conditions. In *Castellaniella defragrans* the protein is expressed as a precursor protein with a signal peptide for a periplasmatic location which is cleaved after transport through the membrane. The enzyme is classified as EC 4.2.1.127. A linalool dehydratase-isomerase has the capacity to catalyze the following reaction under anaerobic conditions:

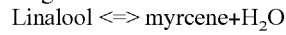
Linalool <=> myrcene+$H_2O$

This activity can, e.g., be measured with an assay as described in Brodkorb et al. (loc. cit.). In such an assay, vials are prewarmed at 35° C., anoxic protein solution is transferred into the vials and DTT is added to 2 mM. The reaction mixtures are sealed with a butyl septum and the headspace is flushed with $CO_2/N_2$ (10/90 (v/v)). The reaction is started by adding a distinct concentration of linalool and incubated at 35° C. The conversion of linalool into myrcene is assessed by investigating the production of myrcene, e.g. by gas chromatography.

In a preferred embodiment, a linalool dehydratase-isomerase also has the capacity to catalyze the isomerisation of geraniol into linalool under anaerobic conditions:

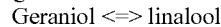
Geraniol <=> linalool

This activity can, e.g., be measured with an assay as described in Brodkorb et al. (loc. cit.). In such an assay, vials are prewarmed at 35° C., anoxic protein solution is transferred into the vials and DTT is added to 2 mM. The reaction mixtures are sealed with a butyl septum and the headspace is flushed with $CO_2/N_2$ (10/90 (v/v)). The reaction is started by adding a distinct concentration of geraniol and incubated at 35° C. The conversion of geraniol into linalool is assessed by investigating the production of myrcene, i.e. the product of the second reaction catalyzed by the enzyme, e.g. by gas chromatography.

Geraniol, linalool and myrcene are acyclic $C_{10}$-terpenoids produced by plants, belonging to the class of allylalcohols and hydrocarbons, respectively. Lüddecke and Harder (Z. Naturforsch. 66c (2011), 409-412) reported on a high substrate specificity of linalool dehydratase-isomerase. The inventors now surprisingly found that linalool dehydratase-isomerase can act on compounds of the formula $C_nH_{2n}O$, with 3<n<7, and can convert them into conjugated dienes. In the appended Examples this is shown for the conversion of but-2-en-1-ol (crotyl alcohol) into butadiene, of but-3-en-2-ol into butadiene, of 3-methylbut-2-en-1-ol (prenol) into isoprene, of 3-methylbut-3-en-1-ol (isoprenol) into isoprene and of 2-methylbut-3-en-2-ol into isoprene. Thus, the present inventors could show that linalool dehydratase-isomerase can unexpectedly also convert alkenols which are much shorter than its natural substrates despite of the reported high substrate specificity.

An example of a sequence of an alkenol dehydratase which can be employed in the method according to the present invention is given in SEQ ID NO: 1 (FIG. 6). A sequence for an alkenol dehydratase is also accessible in the UniProtKB/TrEMBL database under accession number E1XUJ2. These sequences represent an alkenol dehydratase which is classified as a linalool dehydratase-isomerase. In a preferred embodiment the method according to the present invention makes use of an alkenol dehydratase comprising the amino acid sequence shown in SEQ ID NO: 1 or a sequence which is at least x % identical to SEQ ID NO: 1 and which is able to catalyze the conversion of a compound responding to the general formula $C_nH_{2n}O$ into $C_nH_{2n-2}+H_2O$, with 3<n<7, with x being an integer between 30 and 100, preferably 35, 40, 45, 50, 55, 60, 65, 70, 75, 80, 85, 90, 91, 92, 93, 94, 95, 96, 97, 98 or 99.

The term "alkenol dehydratase" as used in the present invention therefore refers to an enzyme which shows the above indicated degree of sequence identity with SEQ ID NO:1 and which can catalyze the conversion of a compound responding to the general formula $C_nH_{2n}O$ into $C_nH_{2n-2}+H_2O$, with 3<n<7. By using the sequence of SEQ ID NO:1 or corresponding encoding nucleotide sequences, it is possible for the skilled person to identify further alkenol dehydratases which can catalyze the above indicated conversion.

Preferably, the degree of identity is determined by comparing the respective sequence with the amino acid sequence of SEQ ID NO:1. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

Moreover, if the term "homology" is used in the context of the present invention, this term preferably means "sequence identity".

As described above, the alkenol dehydratase which is referred to as a "linalool dehydratase-isomerase" identified in *Castellaniella defragrans* (formerly *Alcaligenes defragrans*) has a signal peptide ensuring transport into the periplasmatic space. In a preferred embodiment, the method according to the present invention employs an enzyme which does not show such a signal sequence. It is shown in the Examples that disruption of the signal peptide by insertion of a his-tag does not hamper the expression of the enzyme in *E. coli* and leads to the intracellular production of an active protein.

The alkenol dehydratase, such as a linalool dehydratase-isomerase, employed in the process according to the invention can be a naturally occurring alkenol dehydratase or it can be an alkenol dehydratase which is derived from a naturally occurring alkenol dehydratase such as a linalool dehydratase-isomerase, e.g. by the introduction of mutations or other alterations which, e.g., alter or improve the enzymatic activity, the stability, in particular thermal stability etc.

The term "linalool dehydratase-isomerase" or "a protein/enzyme having the activity of a linalool dehydratase-isomerase" in the context of the present application also covers enzymes which are derived from a linalool dehydratase-isomerase, which are capable of catalyzing the conversion of a compound responding to the general formula $C_nH_{2n}O$ into $C_nH_{2n-2}+H_2O$, with 3<n<7, but which only have a low affinity to their natural substrates, i.e. geraniol, linalool and/or myrcene, or do no longer accept their natural substrates. Such a modification of the preferred substrate allows to improve the conversion of a compound responding to the general formula $C_nH_{2n}O$ into $C_nH_{2n-2}+H_2O$, with 3<n<7, and to reduce the production of possibly occurring unwanted by-products. Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution", DNA shuffling or in vivo evolution.

For example, for genetic engineering in prokaryotic cells, a nucleic acid molecule encoding a linalool dehydratase-isomerase can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting linalool dehydratase-isomerase variants are then tested for their enzymatic activity and in particular for their capacity to prefer a compound responding to the general formula $C_nH_{2n}O$, with 3<n<7, as a substrate rather than, e.g. geraniol, linalool and/or myrcene.

Such methods for identifying variants with improved enzymatic properties as regards the production of a conjugated diene compound may also be carried out in the presence of a cofactor which allows for a steric and/or electronic complementation in the catalytic site of the enzyme due to the fact that the a compound responding to the general formula $C_nH_{2n}O$, with 3<n<7, is shorter than the natural substrates.

In a preferred embodiment the alkenol dehydratase employed in a method according to the invention shows a high thermal stability. Such an enzyme can be obtained by routine methods involving, e.g. randomly mutating a nucleic acid sequence encoding an alkenol dehydratase and screening the obtained mutants for a higher thermal stability. Preferably, the alkenol dehydratase is stable and enzymatically active at temperatures of 68° C. or higher. Since the boiling point of dimethylbutadiene is 68° C. at atmospheric pressure, using such an enzyme and carrying out the method according to the invention at a temperature of 68° C. or higher has the advantage that the dimethylbutadiene degasses out of the reaction and can easily be recovered from the gaseous phase.

The modified version of the alkenol dehydratase, e.g. a variant accepting or preferring a compound responding to the general formula $C_nH_{2n}O$, with 3<n<7, as a substrate but having a low affinity to its natural substrates or no longer accepting its natural substrates or a variant with a higher thermal stability, may be derived from a naturally occurring alkenol dehydratase, such as a linalool dehydratase-isomerase, or from an already modified, optimized or synthetically prepared alkenol dehydratase.

The method according to the invention can be carried out in vitro, e.g. in the presence of isolated enzyme or of cell lysates comprising the enzyme or partially purified enzyme preparations. In vitro preferably means in a cell-free system.

In one embodiment, the enzyme employed in the method is used in purified form to convert a compound responding to the general formula $C_nH_{2n}O$ into $C_nH_{2n-2}+H_2O$, with 3<n<7. However, such a method may be costly, since enzyme and substrate production and purification costs are high.

Thus, in another preferred embodiment, the enzymes employed in the method are present in the reaction as a non-purified extract, or else in the form of non-lysed bacteria, so as to economize on protein purification costs. However, the costs associated with such a method may still be quite high due to the costs of producing and purifying the substrates.

In an in vitro reaction the enzymes, native or recombinant, purified or not, are incubated in the presence of the substrate in physicochemical conditions allowing the enzymes to be active, and the incubation is allowed to proceed for a sufficient period of time allowing production of the diene. At the end of the incubation, one optionally measures the presence of the diene compound by using any detection system known to one of skill in the art such as gas chromatography or colorimetric tests for measuring the formation such compounds.

In a particularly preferred embodiment of the invention the method is carried out in vitro and the enzyme is immobilized. Means and methods for immobilizing enzymes on different supports are well-known to the person skilled in the art.

In another preferred embodiment the method according to the invention is carried out in culture, in the presence of an organism, preferably a microorganism, producing the enzyme. Thus, in such an embodiment of the invention, an organism, preferably a microorganism, that produces an alkenol dehydratase, such as a linalool dehydratase-isomerase, is used. In a preferred embodiment, the (micro)organism is recombinant in that the enzyme produced by the host is heterologous relative to the production host. The method can thus be carried out directly in the culture medium, without the need to separate or purify the enzymes. In an especially advantageous manner, a (micro)organism is used having the natural or artificial property of endogenously producing a compound responding to the general formula $C_nH_{2n}O$, with 3<n<7, and also expressing or overexpressing an alkenol dehydratase, such as a linalool dehydratase-isomerase, natural or modified, so as to produce the diene compound directly from a carbon source present in solution.

For example, the method according to the invention can be carried out by using microorganisms which produce a compound responding to the general formula $C_nH_{2n}O$, with 3<n<7. For example, Perez et al. (Phytochemistry 19 (1980), 183-187) describe enzymes from Citrus sinensis which are able to hydrolyze allylic phosphates, e.g. a prenyl diphosphatase (EC 3.1.7.1) which can convert prenol diphosphate into prenol and diphosphate. Nucleic acid sequences encoding such enzymes can be introduced into microorganisms which produce the corresponding substrate so as to be able to produce prenol. Moreover, Withers et al. (Appl. Environ. Microbiol. 73 (2007), 6277-6283) have described, for example, *E. coli* cells which have been engineered with the mevalonate-based isopentenyl pyrophosphate biosynthetic pathway and which also expressed the nudF gene of *Bacillus subtilis* strain 6,051. The protein encoded by the nudF gene acts directly on prenyl diphosphate precursors and leads to the production of isopentenol (isoprenol).

Thus, in one embodiment of the method according to the present invention it is preferred to use a microorganism which is capable of producing a compound responding to the general formula $C_nH_{2n}O$, with $3<n<7$, and which has been genetically engineered such that it (over)expresses an alkenol dehydratase, said alkenol dehydratase preferably originating from an organism different from the host microorganism. The genetic modification can consist, e.g. in integrating the corresponding gene encoding the alkenol dehydratase into the chromosome, expressing the enzyme from a plasmid containing a promoter upstream of the enzyme-coding sequence, the promoter and coding sequence preferably originating from different organisms, or any other method known to one of skill in the art. Alternatively, other bacteria or yeasts may have specific advantages and can be chosen. For instance, a yeast such as *Saccharomyces cerevisiae*, an extremophilic bacterium such as *Thermus thermophilus*, or anaerobic bacteria from the family Clostridiae, microalgae, or photosynthetic bacteria can be used.

It is also conceivable to isolate the genes encoding the proteins which are responsible for the synthesis of a compound responding to the general formula $C_nH_{2n}O$, with $3<n<7$, and to introduce these genes into another organisms, in particular a microorganism, such as e.g. *E. coli*, *Saccharomyces* or *Pichia*, an extremophilic bacterium such as *Thermus thermophilus*, or anaerobic bacteria from the family Clostridiae, microalgae, or photosynthetic bacteria.

In a preferred embodiment, the (micro)organism) used in the method according to the invention is a (micro)organism which is genetically modified so as to contain a nucleic acid molecule encoding an alkenol dehydratase. Such a nucleic acid molecule encoding an alkenol dehydratase as described above can be used alone or as part of a vector. The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Furthermore, the introduction of mutations into the polynucleotides encoding an enzyme as defined above allows the gene expression rate and/or the activity of the enzymes encoded by said polynucleotides to be optimized, e.g. as regards thermal stability.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

The polynucleotide introduced into a (micro)organism is expressed so as to lead to the production of a polypeptide having the activity described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The coding region encoding the alkenol dehydratase may be modified in ways known to the person skilled in the art. It is, e.g., possible to insert tags which simplify the purification of the protein such as a his-tag (see Example 1). Moreover, it is also possible to delete or disrupt the signal sequence of the enzyme which ensures localization in the periplasma thereby allowing the protein to be produced intracellularly. It is also possible to attach to the coding region a secretion signal allowing secretion of the protein into the culture medium.

It is also possible to express the alkenol dehydratase as a fusion protein in which the alkenol dehydratase is fused to another polypeptide moiety, e.g. another enzyme.

The transformation of the host cell with a polynucleotide or vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The organisms used in the invention can be prokaryotes or eukaryotes, preferably, they are microorganisms. The term "microorganism" in the context of the present invention refers to bacteria, as well as to fungi, such as yeasts, and also to algae and archaea. The term "microorganism" also includes plant cells or animal cells. In a particular embodiment the microorganisms are bacteria. Preferred bacteria to be employed in the process according to the invention are bacteria of the genus *Bacillus, Clostridium, Corynebacterium, Pseudomonas, Zymomonas, Methylobacter* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum*.

In another preferred embodiment, the microorganisms are recombinant bacteria, preferably of the genus *Escherichia*, having been modified so as to endogenously produce a compound responding to the general formula $C_nH_{2n}O$, with $3<n<7$, and converting it to a diene compound as described herein above.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum*.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis* or *Pichia pastoris*.

In a particularly preferred embodiment the microorganism is a recombinant fungus, preferably a yeast producing a compound responding to the general formula $C_nH_{2n}O$, with $3<n<7$, and converting it to a diene compound as described herein above.

In another preferred embodiment, the method according to the invention makes use of a photosynthetic microorganism expressing an alkenol dehydratase. Preferably, the microorganism is a photosynthetic bacterium, or a microalgae. Even more preferably such a microorganism has the natural or artificial property of endogenously producing compound responding to the general formula $C_nH_{2n}O$, with $3<n<7$. In this case the microorganism would be capable of producing a diene directly from $CO_2$ present in solution.

In another preferred embodiment the method according to the invention makes use of a multicellular organism expressing an alkenol dehydratase. Examples for such organisms are plants or animals.

In one embodiment, the method involves cultivating microorganisms in standard culture conditions (30-37° C. at 1 atm, in a fermenter allowing aerobic growth of the bacteria). Butadiene and isoprene have a boiling point of −4° C. and 34° C., respectively, and would already be in a gaseous state if a temperature of 34° C. or higher is chosen for the cultivation. In a preferred embodiment, the method involves cultivating microorganisms under non-standard conditions, preferably at a higher temperature to correspond to the culture conditions of thermophilic organisms. This embodiment has the advantage that even those dienes which have a higher boiling point, in particular dimethylbutadiene (with a boiling point of 68° C.) would degas out of the culture and could be easily collected from the gaseous phase. Thus, in particular in those embodiments of the method according to the invention in which dimethylbutadiene is produced, the microorganism is a thermophilic microorganism which can be cultivated at temperatures of 68° C. or higher.

In a further preferred embodiment, the method according to the invention making use of a microorganism is carried out such that the microorganism is immobilized on a support.

In a further preferred embodiment the method of the invention is carried out in microaerophilic conditions. This means that the quantity of injected air is limiting so as to minimize residual oxygen concentrations in the gaseous effluents containing the produced diene compound.

In another preferred embodiment the method according to the invention is carried out under conditions so that the produced diene is degassing out of the reaction. This has the advantage that the thermodynamic equilibrium of the reaction is shifted toward production of the conjugated diene. It is preferred that the method furthermore comprises the step of collecting the gaseous diene. Thus, in a preferred embodiment, the method is carried out in the presence of a system for collecting the produced diene under gaseous form during the reaction.

In a particular embodiment, the method also comprises detecting the produced diene (butadiene, isoprene or dimethylbutadiene) which is present in the gaseous phase. The presence of the diene to be produced in an environment of air or another gas, even in small amounts, can be detected by using various techniques and in particular by using gas chromatography systems with infrared or flame ionization detection, or by coupling with mass spectrometry.

The present invention also relates to the use of an organism which produces an alkenol dehydratase, such as a linalool dehydratase-isomerase, for the conversion of a compound responding to the general formula $C_nH_{2n}O$ into $C_nH_{2n-2}$+ $H_2O$, with $3<n<7$, as described herein above in connection with the method according to the invention. In a preferred embodiment such an organism is a recombinant organism in the sense that it is genetically modified due to the introduction of at least one nucleic acid molecule encoding an alkenol dehydratase, such as a linalool dehydratase-isomerase. Preferably such a nucleic acid molecule is heterologous with regard to the organism which means that it does not naturally occur in said organism.

In a preferred embodiment such an organism is an organism which produces a compound responding to the general formula $C_nH_{2n}O$, with $3<n<7$.

The present invention also relates to the use of an alkenol dehydratase, such as a linalool dehydratase-isomerase, for the conversion of a compound responding to the general formula $C_nH_{2n}O$ into $C_nH_{2n-2}$+$H_2O$, with $3<n<7$, as described herein above in connection with the method according to the invention.

Moreover, the present invention also relates to a composition comprising an organism which produces an alkenol dehydratase and a compound responding to the general formula $C_nH_{2n}O$, with $3<n<7$. The present invention also relates to a composition comprising an alkenol dehydratase, such as a linalool dehydratase-isomerase, and a compound responding to the general formula $C_nH_{2n}O$, with $3<n<$ As regards the preferred embodiments of the different components recited, the same applies as has been set forth above in connection with the method according to the invention.

FIG. 1 shows schematically the primary allyl alcohols (PRA) responding to the general formula $C_nH_{2n}O$, with $3<n<7$. In particular shown are: Substrate/Systematic name/ Formula/Category/$R^1$/$R^2$/Product FIG. 2 shows schematically the secondary and tertiary allyl alcohols (STA) responding to the general formula $C_nH_{2n}O$, with $3<n<7$. Substrate/Systematic name/Formula/Category/ $R^1$/$R^2$/Product FIG. 3 shows schematically the primary homoallyl alcohols (PHA) responding to the general formula $C_nH_{2n}O$, with $3<n<7$. Substrate/Systematic name/Formula/Category/$R^1$/ $R^2$/Product FIG. 4 shows a schematic overview over the conversion of the above mentioned PRA, PHA and STA compounds into a conjugated diene according to the method of the present invention.

FIG. 6 shows the amino acid sequence of the linalool dehydratase-isomerase from *Castellaniella defragrans* (formerly *Alcaligenes defragrans*).

Other aspects and advantages of the invention will be described in the following examples, which are given for purposes of illustration and not by way of limitation.

EXAMPLES

Example 1

Cloning and Expression in *E. coli* of the Gene for Linalool Dehydratase-Isomerase Cloning and Bacterial Culture The sequence of linalool dehydratase-isomerase inferred from the genome of *Castellaniella defragrans* (formerly *Alcaligenes defragrans*) was generated by oligonucleotide concatenation to fit the codon usage of *E. coli*. A stretch of 6 histidine codons was inserted after the methionine initiation codon to provide an affinity tag for purification. The gene thus synthesized was cloned in a pET25b(+) expression vector (the vector was constructed by GeneArt AG). Competent *E. coli* BL21(DE3) cells (Novagen) were transformed with this vector according to the heat shock procedure. As negative control, *E. coli* BL21(DE3) strain was transformed with empty vector. The transformed cells were grown with shaking (160 rpm) on ZYM-5052 auto-induction medium (Studier F W, *Prot. Exp. Pur.* 41 (2005), 207-234) for 6 hours at 37° C. and protein expression was continued at 18° C. overnight (approximately 12 hours). The cells were collected by centrifugation at 4° C., 10,000 rpm for 20 min and the pellets were frozen at −80° C.

Preparation of Cell Lysate

The pellets from 100 ml of culture cells were thawed on ice and resuspended in 4 ml of 50 mM Tris-HCl pH 7.5. 10 µl of lysonase (Novagen) were then added. Cells were incubated for 10 minutes at room temperature and then returned to ice for 20 minutes. Protein concentration was determined using the Bradford method (Biorad).

Example 2

1,3-butadiene Production from (2E)-2-buten-1-ol (Trans Crotyl Alcohol)

Figure 1:
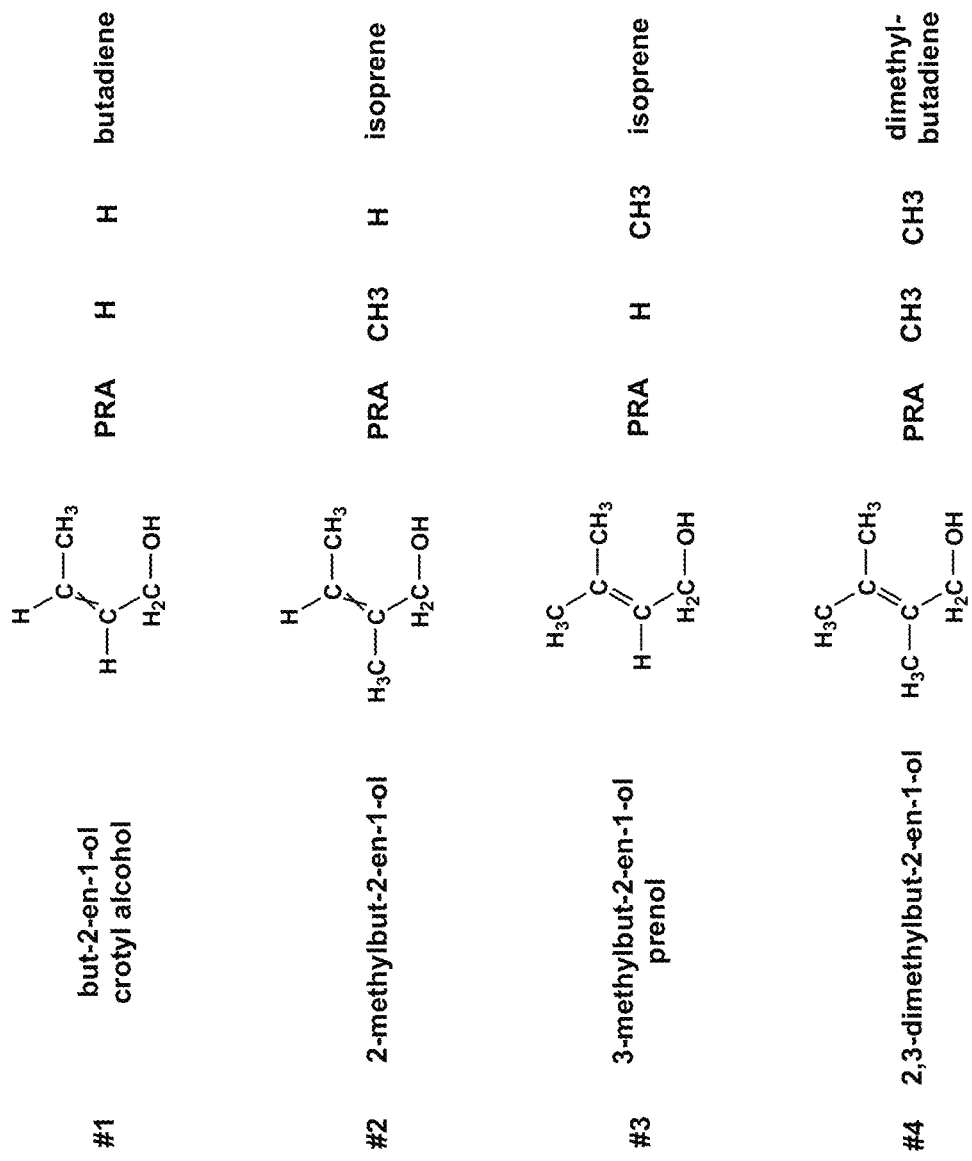
Figure 4:
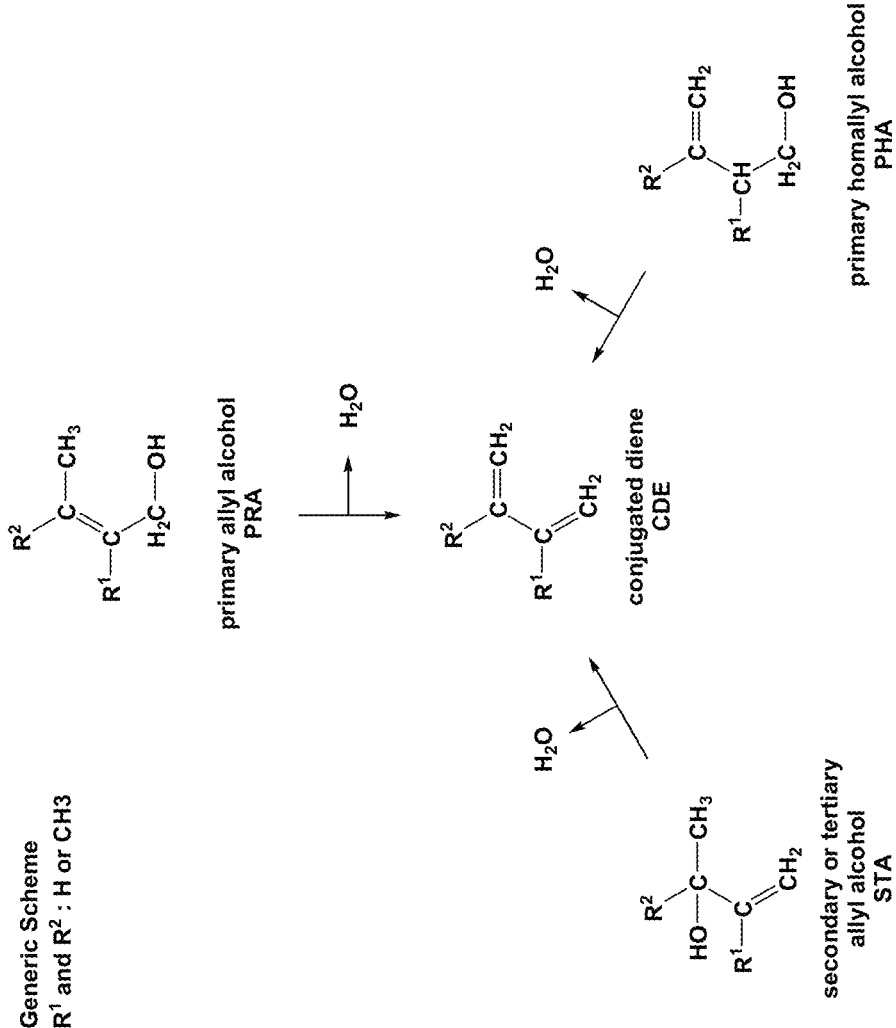
Figure 5:
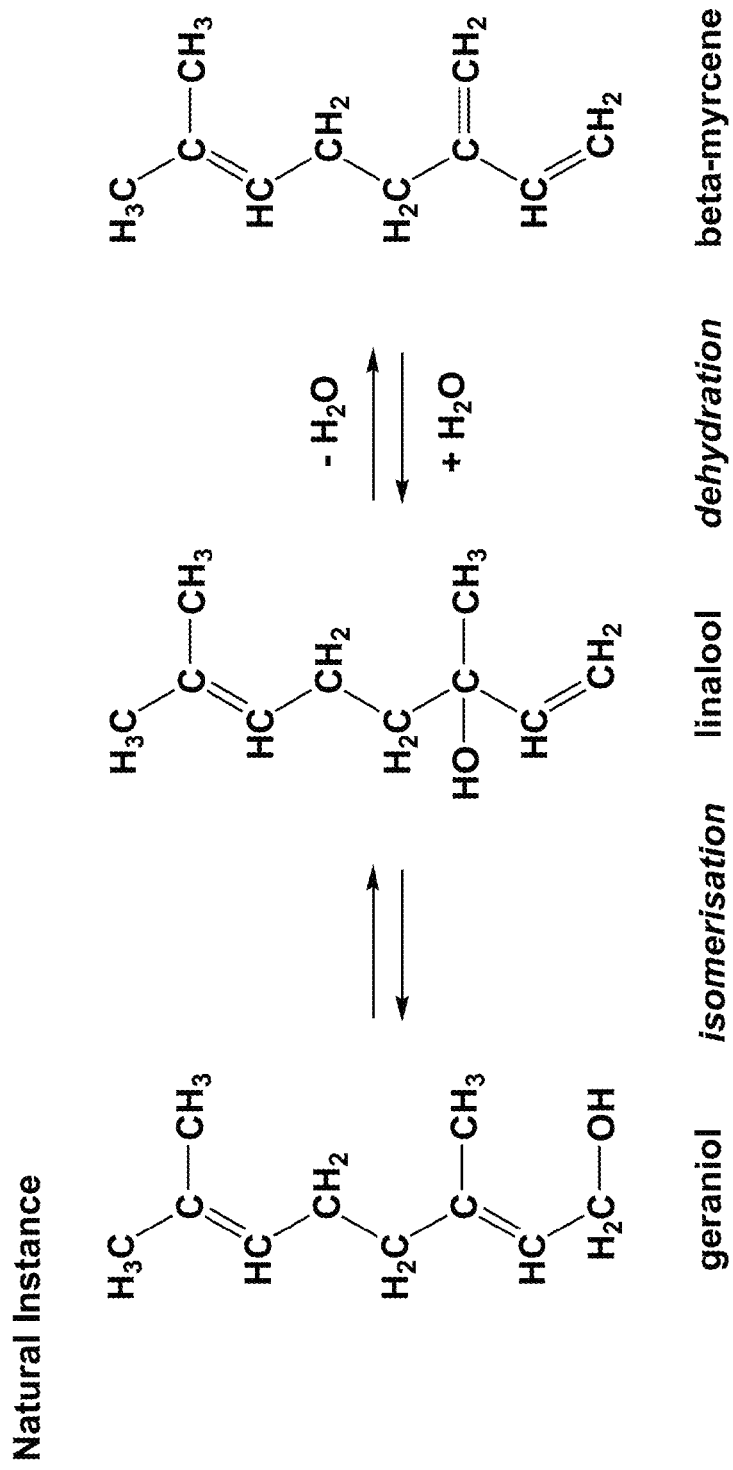
FIG. 5 shows an overview of the reactions catalyzed by linalool dehydratase-isomerase.
Figure 7:
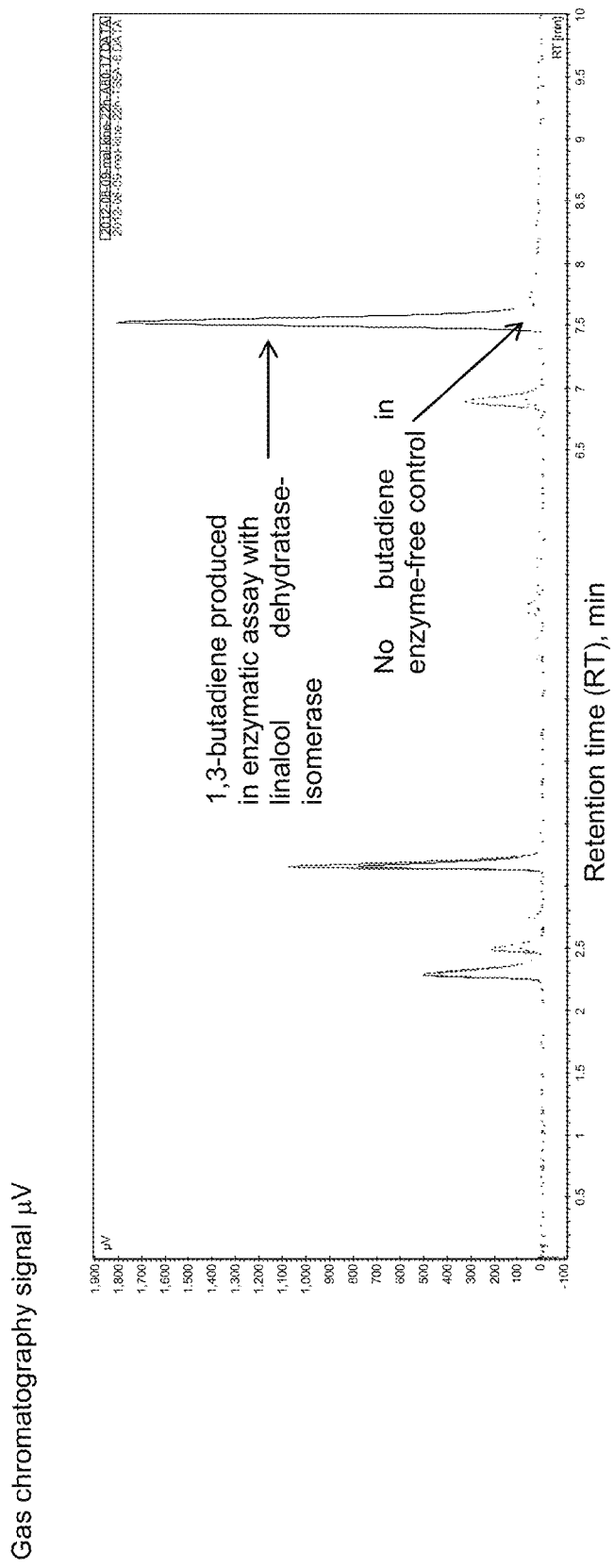
FIG. 7 shows the GC/FID chromatograms obtained for enzymatic (black) and enzyme-free (red) assays with 80 mM trans crotyl alcohol after 22 hours incubation.

The enzymatic assays were carried out under the following conditions:
50 mM Tris HCl pH 7.5
2 mM D,L-Dithiothreitol
0-80 mM (2E)-2-buten-1-ol (trans crotyl alcohol)
The pH was adjusted to 7.5
0.25 ml of cell lysate containing recombinant linalool dehydratase-isomerase was added to 0.5 ml of reaction mixture. An enzyme-free control reaction containing lysate of *E. coli* cells transformed with empty vector was carried out in parallel. Assays were incubated at 37° C. for 1-22 hours in a 2 ml sealed glass vial (Interchim) with shaking. One ml of the headspace phase was then collected and injected into a gas chromatograph Varian 450-GC equipped with a flame ionization detector (FID). Nitrogen was used as carrier gas with a flow rate of 1.5 ml/min. Volatile compounds were chromatographically separated on Rt-Alumina Bond/Na$_2$SO$_4$ column (Restek) using an isothermal mode at 130° C. The enzymatic reaction product was identified by comparison with 1,3-butadiene standard (Sigma). Under these GC conditions, the retention time for butadiene was 7.6 min. A significant production of 1,3-butadiene was observed in enzymatic assay with linalool dehydratase-isomerase. No butadiene signal was observed in enzyme-free control assay (FIG. 7). The turnover number for this conversion amounted to about $3 \times 10^{-5}$ s$^{-1}$ substrate molecule per enzyme active site.

Example 3

1,3-butadiene Production from 3-buten-2-ol

Figure 8:
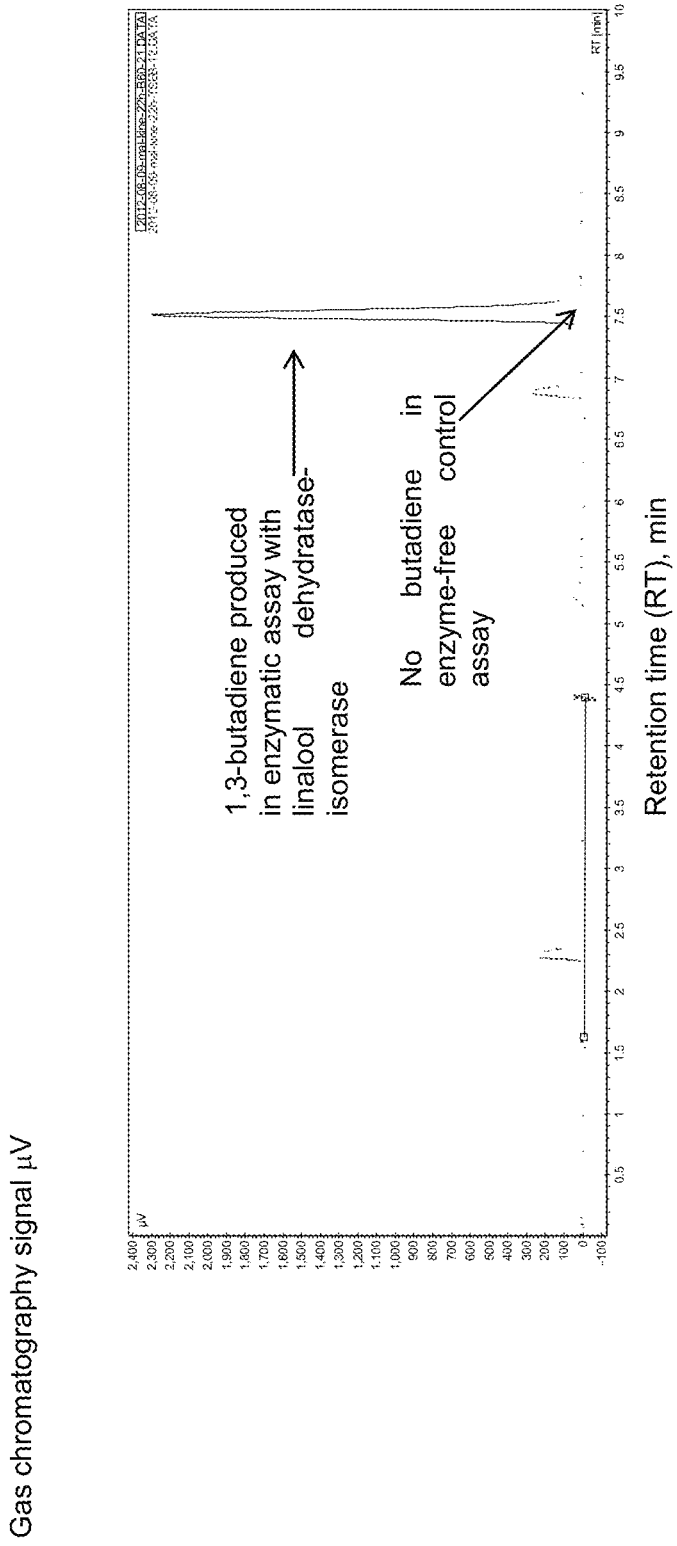
FIG. 8 shows the GC/FID chromatograms obtained for enzymatic (black) and enzyme-free (red) assays with 80 mM 3-buten-2-ol after 22 hours incubation.

The enzymatic assays were carried out under the following conditions:
  50 mM Tris HCl pH 7.5
  2 mM D,L-Dithiothreitol
  0-80 mM 3-buten-2-ol
  The pH was adjusted to 7.5
  0.25 ml of cell lysate containing recombinant linalool dehydratase-isomerase was added to 0.5 ml of reaction mixture. An enzyme-free control reaction containing lysate of *E. coli* cells transformed with empty vector was carried out in parallel. Assays were incubated at 37° C. for 1-22 hours in a 2 ml sealed glass vial (Interchim) with shaking. 1,3-butadiene production was analyzed by GC/FID procedure as described in example 2. A significant production of 1,3-butadiene was observed in enzymatic assay with linalool dehydratase-isomerase. No butadiene signal was observed in enzyme-free control assay (FIG. 8). The turnover number for this conversion amounted to about $10^{-4}$ s$^{-1}$ substrate molecule per enzyme active site.

Example 4

2-methyl-1,3-butadiene (isoprene) production from 3-methyl-2-buten-1-ol (prenol)

The enzymatic assays were carried out under the following conditions:
  50 mM Tris HCl pH 7.5
  2 mM D,L-Dithiothreitol
  0-80 mM 3-methyl-2-buten-1-ol (prenol)
  The pH was adjusted to 7.5
  0.25 ml of cell lysate containing recombinant linalool dehydratase-isomerase was added to 0.5 ml of reaction mixture. An enzyme-free control reaction containing lysate of *E. coli* cells transformed with empty vector was carried out in parallel. Assays were incubated at 37° C. for 1-22 hours in a 2.0 ml sealed glass vial (Interchim) with shaking. 100 µl of the headspace phase was then collected and injected into a gas chromatograph Varian 450-GC equipped with a flame ionization detector (FID). Volatiles compounds from headspace phase were separated on Rtx-1 column (Restek) using nitrogen as carrier gas with a flow rate of 1.5 ml/min. The oven cycle for each sample was 100° C. for 4 minutes, increasing temperature at 20° C./minute to a temperature of 130° C., and hold at 130° C. for 1.5 minutes. The total run time was 7 min. The enzymatic reaction product was identified by comparison with isoprene standard (Sigma). Under these GC conditions, the retention time for isoprene was 3.08 min. A significant production of isoprene was observed in enzymatic assay with linalool dehydratase-isomerase. An insignificant signal of isoprene corresponding to spontaneous decomposition of prenol was observed in enzyme-free control assay (Table 1). The turnover number for this conversion amounted to about $3 \times 10^{-4}$ s$^{-1}$ substrate molecule per enzyme active site.

TABLE 1

| Isoprene production after 22 hours incubation in assays with 80 mM prenol.. | |
|---|---|
| Assay | Isoprene peak area, arbitrary units |
| Enzymatic assay with linalool dehydratase-isomerase | 29705.4 |
| Enzyme-free control assay | 7.5 |

Example 5

2-methyl-1,3-butadiene (isoprene) production from 3-methyl-3-buten-1-ol (isoprenol)

Figure 9:
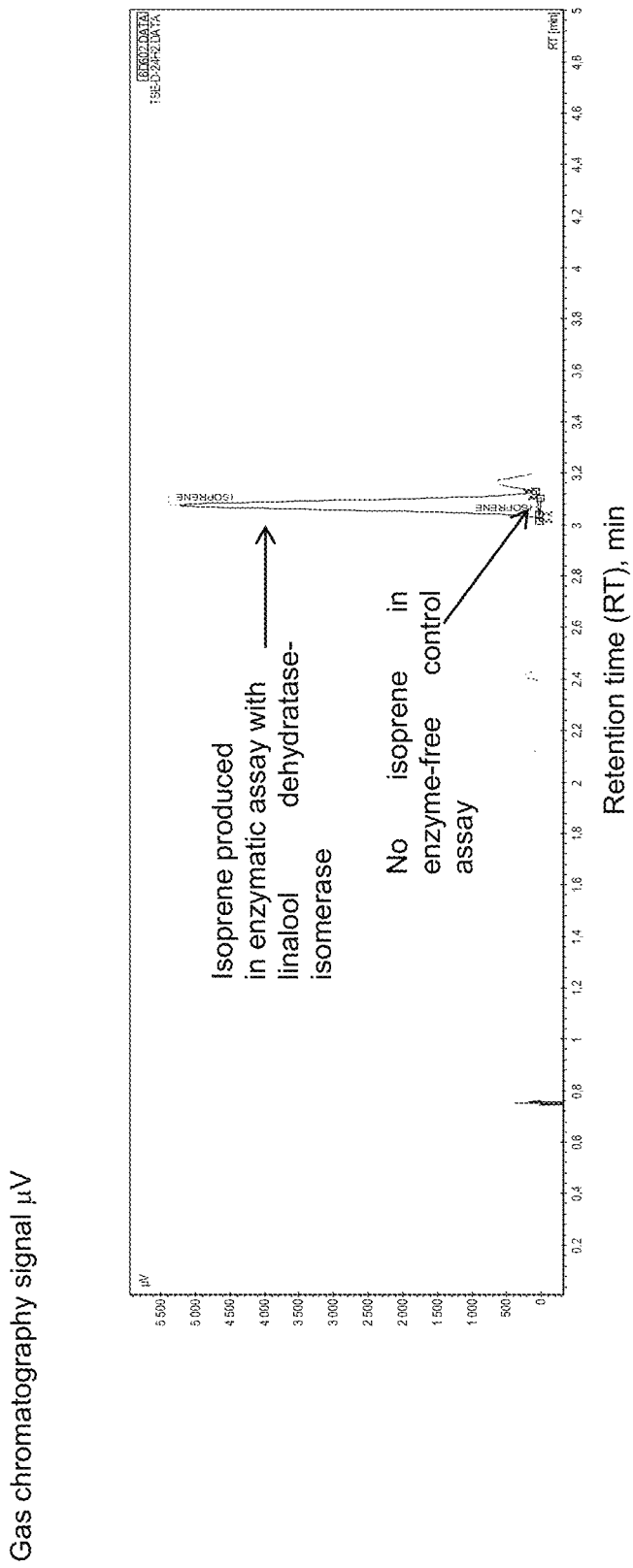
FIG. 9 shows the GC/FID chromatograms obtained for enzymatic (black) and enzyme-free (blue) assays with 80 mM isoprenol after 22 hours incubation.

The enzymatic assays were carried out under the following conditions:
  50 mM Tris HCl pH 7.5
  2 mM D,L-Dithiothreitol
  0-80 mM 3-methyl-3-buten-1-ol (isoprenol)
  The pH was adjusted to 7.5
  0.25 ml of cell lysate containing recombinant linalool dehydratase-isomerase was added to 0.5 ml of reaction mixture. An enzyme-free control reaction containing lysate of *E. coli* cells transformed with empty vector was carried out in parallel. Assays were incubated at 37° C. for 1-22 hours in a 2 ml sealed glass vial (Interchim) with shaking. Isoprene production was analyzed by GC/FID procedure as described in example 4. A significant production of isoprene was observed in enzymatic assay with linalool dehydratase-isomerase. No isoprene signal was observed in enzyme-free control assay (FIG. 9). The turnover number for this conversion amounted to about $3 \times 10^{-5}$ s$^{-1}$ substrate molecule per enzyme active site.

Example 6

2-methyl-1,3-butadiene (isoprene) production from 2-methyl-3-buten-2-ol

Figure 10:
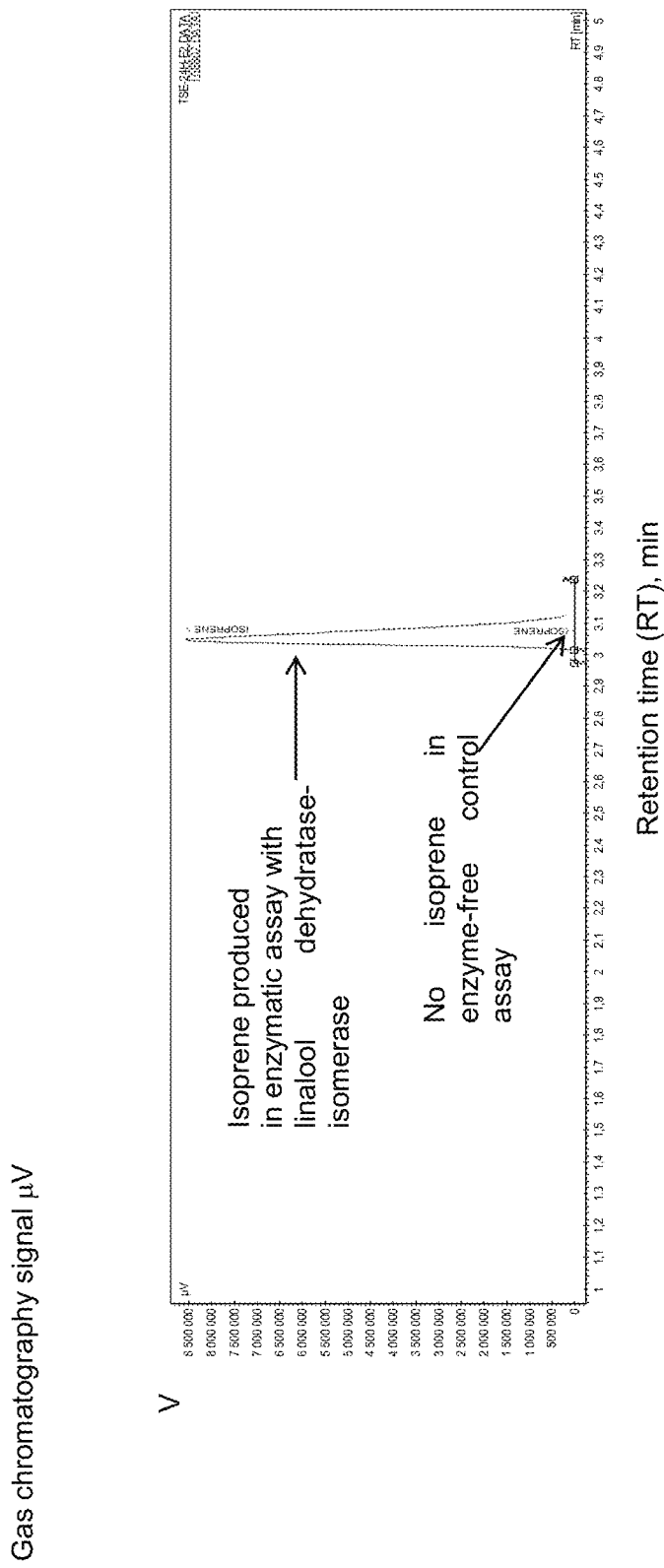
FIG. 10 shows the GC/FID chromatograms obtained for enzymatic (red) and enzyme-free (black) assays with 80 mM 2-methyl-3-buten-2-ol after 22 hours incubation.

The enzymatic assays were carried out under the following conditions:
  50 mM Tris HCl pH 7.5
  2 mM D,L-Dithiothreitol
  0-80 mM 2-methyl-3-buten-2-ol
  The pH was adjusted to 7.5
  0.25 ml of cell lysate containing recombinant linalool dehydratase-isomerase was added to 0.5 ml of reaction mixture. An enzyme-free control reaction containing lysate of *E. coli* cells transformed with empty vector was carried out in parallel.
  Assays were incubated at 37° C. for 1-22 hours in a 2 ml sealed glass vial (Interchim) with shaking. Isoprene production was analyzed by GC/FID procedure as described in example 4. A significant production of isoprene was observed in enzymatic assay with linalool dehydratase-isomerase. No isoprene signal was observed in enzyme-free control assay (FIG. 10). The turnover number for this conversion amounted to about $10^{-3}$ s$^{-1}$ substrate molecule per enzyme active site.

The invention claimed is:

1. A method for producing 1,3-butadiene comprising enzymatically converting an alcohol compound of the general formula $C_4H_8O$ to 1,3-butadiene by using an enzyme at least 70% identical to the amino acid sequence of SEQ ID NO:1, wherein said enzyme has alkenol dehydratase activity.

2. The method of claim 1, wherein the enzyme is at least 80% identical to the amino acid sequence of SEQ ID NO:1.

3. The method of claim 1, wherein the enzyme is at least 90% identical to the amino acid sequence of SEQ ID NO:1.

4. The method of claim 3, wherein the alcohol compound is but-2-en-1-ol.

5. The method of claim 3, wherein the alcohol compound is but-3-en-2-ol.

6. The method of claim 3, wherein the alcohol compound is but-3-en-1-ol.

7. The method of claim 3, wherein said method is carried out in vitro.

8. The method of claim 3, wherein a microorganism produces the enzyme.

9. The method of claim 1, wherein the enzyme is at least 95% identical to the amino acid sequence of SEQ ID NO:1.

10. The method of claim 1, wherein the enzyme is the amino acid sequence of SEQ ID NO:1.

11. The method of claim 10, wherein said method is carried out in vitro.

12. The method of claim 10, wherein a microorganism produces the enzyme.

13. A composition comprising a microorganism which produces an enzyme at least 70% identical to the amino acid sequence of SEQ ID NO:1 and an alcohol compound of the general formula $C_4H_8O$, wherein said enzyme has alkenol dehydratase activity.

14. The composition of claim 13, wherein the enzyme is at least 80% identical to the amino acid sequence of SEQ ID NO:1.

15. The composition of claim 13, wherein the enzyme is at least 90% identical to the amino acid sequence of SEQ ID NO:1.

16. The composition of claim 15, wherein the alcohol compound is but-2-en-1-ol.

17. The composition of claim 15, wherein the alcohol compound is but-3-en-2-ol.

18. The composition of claim 15, wherein the alcohol compound is but-3-en-1-ol.

19. The composition of claim 13, wherein the enzyme is at least 95% identical to the amino acid sequence of SEQ ID NO:1.

20. The composition of claim 13, wherein the enzyme is the amino acid sequence of SEQ ID NO:1.

21. A composition comprising an enzyme at least 70% identical to the amino acid sequence of SEQ ID NO:1 and an alcohol compound of the general formula $C_4H_8O$, wherein said enzyme has alkenol dehydratase activity.

22. The composition of claim 21, wherein the enzyme is at least 80% identical to the amino acid sequence of SEQ ID NO:1.

23. The composition of claim 21, wherein the enzyme is at least 90% identical to the amino acid sequence of SEQ ID NO:1.

24. The composition of claim 23, wherein the alcohol compound is but-2-en-1-ol.

25. The composition of claim 23, wherein the alcohol compound is but-3-en-2-ol.

26. The composition of claim 23, wherein the alcohol compound is but-3-en-1-ol.

27. The composition of claim 21, wherein the enzyme is at least 95% identical to the amino acid sequence of SEQ ID NO:1.

28. The composition of claim 21, wherein the enzyme is the amino acid sequence of SEQ ID NO:1.

* * * * *

UNITED STATES PATENT AND TRADEMARK OFFICE
CERTIFICATE OF CORRECTION

| | | |
|---|---|---|
| PATENT NO. | : 8,703,455 B2 | Page 1 of 1 |
| APPLICATION NO. | : 13/957482 | |
| DATED | : April 22, 2014 | |
| INVENTOR(S) | : Philippe Marliere | |

It is certified that error appears in the above-identified patent and that said Letters Patent is hereby corrected as shown below:

In the Title Page, item (72), the Inventor's name should appear as follows:

Philippe Marliere

In the Title Page, item (73), the assignee name should appear as follows:

Scientist of Fortune, S.A.

Signed and Sealed this
Twenty-fourth Day of May, 2016

Michelle K. Lee
*Director of the United States Patent and Trademark Office*